United States Patent
Zangen et al.

(10) Patent No.: US 9,533,168 B2
(45) Date of Patent: Jan. 3, 2017

(54) UNILATERAL COILS FOR DEEP TRANSCRANIAL MAGNETIC STIMULATION

(71) Applicant: BRAINSWAY, LTD., Jerusalem (IL)

(72) Inventors: Abraham Zangen, Jerusalem (IL); Yiftach Roth, Rechelim (IL)

(73) Assignee: BRAINSWAY, LTD., Jerusalem (IL)

( * ) Notice: Subject to any disclaimer, the term of this patent is extended or adjusted under 35 U.S.C. 154(b) by 205 days.

(21) Appl. No.: 13/772,526

(22) Filed: Feb. 21, 2013

(65) Prior Publication Data

US 2014/0235927 A1    Aug. 21, 2014

(51) Int. Cl.
*A61N 2/02* (2006.01)
*A61N 2/00* (2006.01)

(52) U.S. Cl.
CPC ............... *A61N 2/02* (2013.01); *A61N 2/006* (2013.01)

(58) Field of Classification Search
CPC ............ A61N 2/00–2/12; A61N 1/403; A61N 2005/0647; A61B 2019/2265; A61F 2007/009
USPC ....................................................... 600/9–15
See application file for complete search history.

(56) References Cited

U.S. PATENT DOCUMENTS

| | | | |
|---|---|---|---|
| 4,994,015 A | 2/1991 | Cadwell | |
| 4,996,479 A | 2/1991 | Hoenig | |
| 5,078,674 A | 1/1992 | Cadwell | |
| 5,116,304 A | 5/1992 | Cadwell | |
| 5,738,625 A | 4/1998 | Gluck | |
| 6,066,084 A | 5/2000 | Edrich et al. | |
| 6,179,771 B1 | 1/2001 | Mueller | |
| 6,402,678 B1 | 6/2002 | Fischell et al. | |
| 6,926,660 B2 | 8/2005 | Miller | |
| 7,087,008 B2 | 8/2006 | Fox et al. | |
| 7,407,478 B2 | 8/2008 | Zangen et al. | |
| 7,976,451 B2 | 7/2011 | Zangen et al. | |
| 7,998,053 B2 | 8/2011 | Aho | |
| 8,267,850 B2 | 9/2012 | Schneider et al. | |
| 8,277,371 B2 | 10/2012 | Zangen et al. | |
| 8,388,510 B2 | 3/2013 | Zangen et al. | |
| 8,523,753 B2 | 9/2013 | Schneider et al. | |
| 8,591,392 B2 | 11/2013 | Bentwich et al. | |
| 8,608,634 B2 | 12/2013 | Zangen et al. | |

(Continued)

FOREIGN PATENT DOCUMENTS

EP    0361137    4/1990
EP    0492263    7/1992
(Continued)

OTHER PUBLICATIONS

Bishop, M P., "Intracranial Self-Stimulation in Man", *Science* 140(3565), (1963),394-396.

(Continued)

*Primary Examiner* — Catherine B Kuhlman
(74) *Attorney, Agent, or Firm* — Daniel J. Swirsky; Ricki L. Simon; AlphaPatent Associates Ltd.

(57) ABSTRACT

A coil for transcranial magnetic stimulation which is location-specific for unilateral brain regions is designed with multiple spaced apart stimulating elements having current flow in a first direction, and multiple return elements having current flow in a second direction which is opposite the first direction. The multiple stimulating elements and return elements are distributed on one side of a central axis of the coil.

4 Claims, 13 Drawing Sheets

(56) References Cited

U.S. PATENT DOCUMENTS

| | | | |
|---|---|---|---|
| 8,657,731 | B2 | 2/2014 | Riehl et al. |
| 8,723,628 | B2 | 5/2014 | Mishelevich et al. |
| 2005/0154426 | A1 | 7/2005 | Boveja et al. |
| 2005/0228209 | A1 | 10/2005 | Schneider et al. |
| 2006/0094924 | A1 | 5/2006 | Riehl et al. |
| 2006/0129205 | A1 | 6/2006 | Boveja et al. |
| 2006/0287566 | A1* | 12/2006 | Zangen et al. .......... 600/15 |
| 2007/0293916 | A1 | 12/2007 | Peterchev |
| 2010/0152522 | A1 | 6/2010 | Zangen et al. |
| 2011/0184223 | A1 | 7/2011 | Peterchev |

FOREIGN PATENT DOCUMENTS

| | | |
|---|---|---|
| EP | 0554880 | 8/1993 |
| EP | 0595227 | 5/1994 |
| WO | WO-91/02259 | 2/1991 |
| WO | WO-98/06342 | 2/1998 |
| WO | WO-02/32504 | 4/2002 |
| WO | WO-2010/017249 | 2/2010 |
| WO | WO-2010/067336 | 6/2010 |

OTHER PUBLICATIONS

Branston, N. M., "Analysis of the distribution of currents induced by a changing magnetic field in a volume conductor", *Phys. Med. Biol.* 36(2), (1991),161-168.

Branston, N. M., Tofts P.S., "Magnetic stimulation of a volume conductor produces a negligible component of induced current perpendicular to the surface", J Physiol (Lond). 1990;423:67.

Brasil-Neto, Joaquim P., "Optimal focal transcranial magnetic activation of the human motor cortex: effects of coil orientation, shape of the induced current pulse, and stimulus intensity", *Journal of Clinical Neurophysiology* 9(1), (1992),132-136.

Breiter, Hans C., "Acute effects of cocaine on human brain activity and emotion", *Neuron* 19, (1997),591-611.

Cadwell, John , "Optimizing magnetic stimulator design", *Magnetic Motor Stimulation: Principles and Clinical Experience 43*, (1991),238-248.

Cohen, David , "Developing a more focal magnetic stimulator, Part I: Some basic principles", *Journal of Clinical Neurophysiology* 8(1), (1991),102-111.

Cohen, Leonardo G., "Effects of coil design on delivery of focal magnetic stimulation. Technical considerations", *Electroencephalography and Clinical Neurophysiology 75*, (1990),350-357.

Deng, Zhi-De, "Coil Design Considerations for Deep-Brain Transcranial Magnetic Stimulation (dTMS)", 30th Annual International IEEE EMBS Conference Vancouver, British Columbia, Canada, Aug. 20-24, 2008, 5675-5679.

Eaton, H., "Electric field induced in a spherical volume conductor from arbitrary coils: application to magnetic stimulation and MEG", *Medical and Biological Engineering and Computing 30*, (Jul. 1992),433-440.

Enticott, Peter G. et al, "Deep Repetitive Transcranial Magnetic Stimulation Associated With Improved Social Functioning in a Young Woman With an Autism Spectrum Disorder", (J ECT 2011;27: 41-43).

Fadini, Tommaso et al., "H-coil: Induced electric field properties and input/output curves on healthy volunteers, comparison with a standard figure-of-eight coil", Clinical Neurophysiology 120 (2009) 1174-1182.

George, Mark S., "Transcranial Magnetic Stimulation", *Neurosurgery Clinics of North America 14*, (2003),283-301.

Hallett, Mark , "Transcranial magnetic stimulation and the human brain", *Nature 406*, (Jul. 2000),147-150.

Klein, Ehud , "Therapeutic efficacy of right prefrontal slow repetitive transcranial magnetic stimulation in major depression—a double-blind controlled study", *Arch. Gen. Psychiat. 56*, (1999),315-320.

Kranz, G., "Transcranial magnetic brain stimulation modulates blepharospasm", Neurology 75 (16), (2010), 1465-1471.

Kraus, Karl H., "The use of a cap-shaped coil for transcranial magnetic stimulation of the motor cortex", *Journal of Clinical Neurophysiology 10*,(1993),353-362.

Krause, Laura et al, "The role of medial prefrontal cortex in theory of mind: A deep rTMS study", Behavioural Brain Research [2012, 228(1):87-90].

MacCabee, P. J., "Spatial distribution of the electric field induced in volume by round and figure '8' magnetic coils: relevance to activation of sensory nerve fibers", *Electroencephalography and Clinical Neurophysiology 76*, (1990),131-141.

Paus, Tomas , "Transcranial Magnetic Stimulation during Positron Emission Tomography: A New Method for Studying Connectivity of the Human Cerebral Cortex", *Journal of Neuroscience 17*, (1997),3178-3184.

Ren, Chunye , "A novel electric design for electromagnetic stimulation—the slinky coil", *IEEE Transactions on Biomedical Engineering* 42(9), (Sep. 1995),918-925.

Roth, Yiftach , "A coil design for transcranial magnetic stimulation of deep brain regions", *Journal of Clinical Neurophysiology* 19(4), (2002),361-370.

Ruohonen, J , "Focusing and targeting of magnetic brain stimulation using multiple coils", *Medical and Biological Engineering and Computing*, (1998),297-301.

Thielscher, Axel et al., "Linking Physics with Physiology in TMS: A Sphere Field Model to Determine the Cortical Stimulation Site in TMS", NeuroImage 17, 1117-1130 (2002) doi:10.1006/nimg.2002. 1282.

Tofts, P.S., "The Distribution of Induced Currents in Magnetic Stimulation of the Nervous System", *Phys. Med. Biol.* 35(8), (1990),1119-1128.

Tofts, P.S., "The Measurement of Electric Field, and the Influence of Surface Charge, in Magnetic Stimulation", *Electroencephalography and Clinical Neurophysiology 81*, (1991),238-239.

Yunokuchi, Kazutomo , "Developing a more focal magnetic stimulator, Part II: Fabricating coils and measuring induced current distributions", *Journal of Clinical Neurophysiology* 8(1), (1991),112-120.

Zangen, Abraham , "Transcranial magnetic stimulation of deep brain regions: evidence for efficacy of the H-coil", *Clinical Neurophysiology 116*, (2005),775-779.

Zimmermann, Kuno P., "Slinky coils for neuromagnetic stimulation", *Electroencephalography and Clinical Neurophysiology 101*, (1996),145-152.

* cited by examiner

UNILATERAL COILS FOR DEEP TRANSCRANIAL MAGNETIC STIMULATION

FIELD OF THE INVENTION

The present invention relates to a family of deep transcranial magnetic stimulation (TMS) coils, wherein a stimulating portion of the coils is configured to stimulate an area of a single hemisphere of a brain.

BACKGROUND OF THE INVENTION

Transcranial magnetic stimulation (TMS) is a noninvasive technique used to apply brief magnetic pulses to the brain, or to other human organs, and to thereby activate neuronal structures. The pulses are administered by passing high currents by a stimulator through an electromagnetic coil externally placed upon the patient (for example, placed on the scalp for brain treatment), inducing electrical currents in the underlying tissue, thereby producing a localized axonal depolarization. This technique has become a major tool in central nervous system research, as well as a potentially promising treatment option for various neurobehavioral and neurological disorders.

Most known TMS coils stimulate superficial brain regions in the brain cortex, but the rate of decay of the induced magnetic and electric field as a function of distance from the coil is high. Hence the efficacy of affecting deeper neuronal structures is low. Stimulating deeper neuronal structures may be feasible if the intensity of the induced field is greatly increased. Yet operation at such increased intensity may increase the risk for seizures and for physiological damage to the tissue.

A method for deep brain TMS with minimal stimulation of superficial regions is disclosed in U.S. Pat. No. 7,407,478, wherein deep brain stimulation is made possible while minimizing side effects. The device described therein includes a base and an extension portion, the base having individual windings for individual paths of current flow, and the extension portion designed so as to minimize unwanted stimulation of other regions of the brain.

However, there is a need for more specifically designed coils, which can target particular areas of the brain including deep neuronal structures with minimal effect on other brain regions. Specifically there is a need for coils which can target unilateral brain regions in a certain hemisphere with minimal effect on the contralateral hemisphere. Examples of specific brain regions that may be desired to be stimulated are the right or left insular cortex. Other examples may include right or left medial and lateral prefrontal cortex (PFC), the Broca's area or it's contralateral homologue, the Wernicke's area or its contralateral homologue, the entorhinal cortex, temporal cortex regions such as the fusiform face area (FFA) and the superior temporal sulcus (STS). The coils must induce the desired distribution of the electric field in the brain, and simultaneously induce electric field intensity in the relevant brain tissue which will be feasible for neuronal stimulation with available TMS stimulators for most of the population. The stimulation intensity is routinely calibrated individually for each subject based on his motor threshold. Hence the coil efficiency must guarantee that the motor threshold and stimulation intensity for most of the relevant population is within an acceptable range with respect to available stimulators power outputs. The coils design must be efficient with respect to energy consumption, coil heating rate, compact size and ease of operation.

SUMMARY OF THE INVENTION

There is provided, in accordance with one embodiment of the present invention, a coil for transcranial magnetic stimulation. The coil includes an axis defining a central portion of the body part, a base portion positioned on a side of the axis, the base portion having multiple spaced apart stimulating elements nested within one another and configured to carry electrical current in substantially a first direction, and a return portion positioned on the same side of the axis, the return portion having multiple return elements, wherein each of the multiple return elements corresponds to one of the multiple stimulating elements, and wherein each of the multiple return elements is configured to carry electrical current in substantially a second direction, wherein the second direction is an opposite direction to the first direction, wherein the return portion is spaced a distance away from said base portion.

In embodiments of the present invention, the base portion is complementary to the human head or head portion, or to another body organ. The base has a flexibility that allows it to conform to the relevant body organ (such as the human head or head portion).

The base includes individual elements carrying electric current in one or more common directions, referred to herein as a "main direction." In this main direction, the main physiologic effect (such as neuronal stimulation) is induced in the body organ. The elements are not dense together at a narrow segment, but are rather distributed at various locations around the body organ. In some embodiments the individual elements are evenly distributed across the base. In other embodiments some or all the elements may be grouped in two or more groups with certain distances between the groups. The spacing between adjacent elements may be uniform, variable, periodic or other. In embodiments where some or all the elements are grouped in groups, the spacing between adjacent groups or between a group and an adjacent element, and the breadth of each group, may be uniform across the base, variable, periodic or other. Any combination or arrangement of elements is included within the scope of the invention, with a particular feature being that the elements are not crowded together in a narrow segment.

The individual elements in the base carrying current in the main direction are all or mostly tangential to the relevant body organ (such as a portion of a human skull), at all or a substantial part of their path. In order to optimize the efficacy of activation in deeper brain regions, it is desirable to minimize the non-tangential components of the induced electric field. Since the induced electric field orientation is in general parallel to the orientation of the elements carrying alternating currents, it is desirable to minimize the portions of coil elements which are non-tangential to the body organ (such as a human skull), especially in the base and its vicinity.

Coil elements carrying electric current in a direction opposite to the one or more main directions, are placed remote from the base. These elements are referred to herein as "return elements." In some embodiments, the return elements are located adjacent to other body organs or other portions of a body organ (such as other head regions), relative to the base. These return elements are termed "contacting return elements." In other embodiments, the return elements are located at a certain distance from the body and are not configured to contact the body. These return elements are termed "protruding return elements." In some embodiments, some of the return elements are contacting and some of them are protruding.

In embodiments of the present invention, the base is positioned adjacent to one hemisphere of the brain, either the left hemisphere or the right hemisphere. In embodiments of the invention, the stimulating elements may be adjacent to temporal regions, to frontal regions, to parietal regions, to occipital regions or any combination of the above.

Return elements are located remote from the base. In some embodiments return elements are contacting and adjacent to cortical regions of the contralateral hemisphere relative to the base. In some embodiments all or some of the return elements are contacting and adjacent to cortical regions of the ipsilateral hemisphere relative to the base. In other embodiments return elements are protruding and located at a distance from any brain region. In yet other embodiments some of the return elements are contacting and some are protruding.

The definition of the base relates to the functional elements of the coil carrying electric currents. However, there is no limitation regarding other elements of the device, such as mechanical components, cases and covers. Thus, certain elements of the base may be encased in a case containing additional coil elements such as return elements and other elements.

The coil must induce the desired distribution of the electric field in the brain, and simultaneously induce an electric field intensity in the relevant brain tissue which is high enough to induce neuronal stimulation.

Several features of the coil are important in order to achieve the above goals. These include:

1. Arrangement of the base portion elements. This arrangement must be optimized for each coil design and each specific goal. An interplay between two competing ideals may take place: Better depth penetration profile, namely higher relative electric field in the deeper target brain region compared to superficial region, on one hand, and higher absolute electric field intensity in the target brain region on the other hand. As a non-limiting example, suppose a base portion contains two groups of elements with a certain distance d between them. Increasing d will improve the depth penetration profile but may reduce the absolute field intensity in the target brain region. The intensity must be such that it will enable induction of the desired physiological effect in the target neural structures in the majority of the population with stimulators available in the market. Hence the distance d—as well as other configuration parameters—must be optimized for each coil design.

2. Location of the return portions relative to the base portion. The distance between the portions must be optimized for each design: Too short a distance will lead to reduction of the total induced electric field in the target brain region, due to the effect of the return elements. Too long a distance will require long connecting coil elements and their effect must be taken into account. Furthermore, the coil size must be optimized for easy location, navigation and placement over the head.

3. Location of the return portions relative to the brain. The return elements affect closer brain regions. The location of the return portions must consider their effect on any brain structure and the design must lead to minimal undesired side effects such as motor activation or pain.

4. The type of the return elements. Return elements may be either contacting or protruding as defined above. The ratio between contacting and protruding return elements is very important in various aspects and must be optimized for each specific coil design. In general, protruding elements induce electrostatic charge accumulation on the brain surface. This leads to reduction in the absolute electric field induced in the target brain regions, and also reduction in the relative intensity of the electric field in deeper brain regions compared to superficial regions. On the other hand, contacting elements may increase the effect in adjacent brain regions. Hence a delicate optimization must be performed in each case.

5. The distance of protruding return elements from the head, in coils containing protruding return elements. Longer distance reduces the direct effect of the return elements on the brain, but increases the charge accumulation due to the presence of longer non-tangential coil elements which are connected to the return elements and move them away from the head. A delicate optimization must be performed in each case to account for this effect.

6. The overall coil inductance. The number, length, configuration and packing parameters of the coil windings must be planned to lead to coil inductance in the desired range. Usually the desired range for TMS coils inductance is between 15 and 30 microHenri. Too high inductance may reduce coil efficacy, increase pulse width and is often associated with increased coil resistance, energy consumption and coil heating. Too small inductance may lead to fast rate of change of the electric current which may damage stimulator components.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which.

Figure 1A:
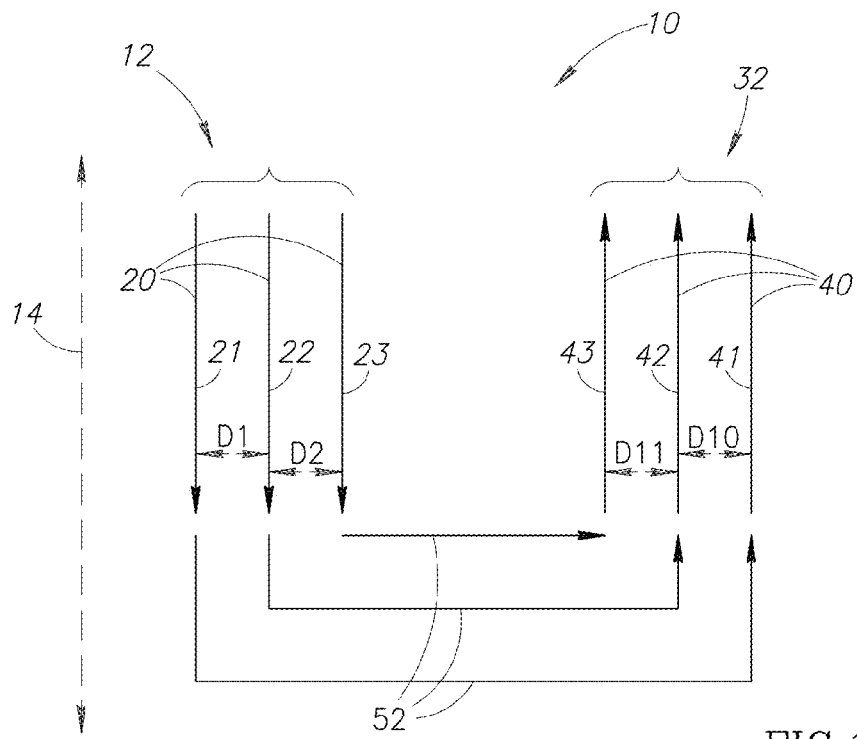
FIGS. 1A and 1B are schematic illustrations showing principles of stimulation for unilateral coils, in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

The present invention is directed to unilateral base coils for deep TMS and methods of use thereof. The principles and operation of systems and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Figure 1B:
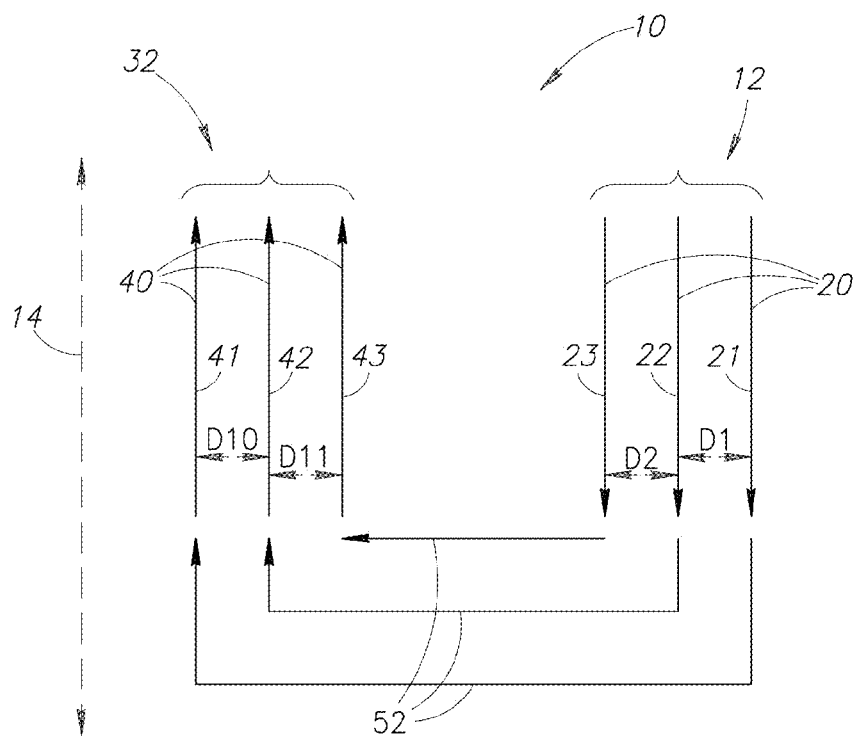

Reference is now made to FIGS. 1A and 1B, which are schematic illustrations showing principles of stimulation for unilateral coils, in accordance with embodiments of the present invention. In the embodiment shown in FIGS. 1A and 1B, a schematic illustration of a unilateral coil depicts the elements of a unilateral coil in accordance with embodiments of the present invention, but does not depict the actual appearance of these elements. As shown in FIGS. 1A and 1B, unilateral coil 10 includes a base portion 12 and a return portion 32.

A central axis 14 defines a portion of coil 10 to be positioned at a mid-point of a body part. It should be readily apparent that central axis 14 may be an imaginary axis or may be a curved axis, and is used herein for descriptive purposes and for geometric orientation. Base portion 12 is positioned either on a right side of central axis 14 or on a left side of central axis 14, but not both. Directions of right side and left side are defined in accordance with anatomical definitions. Thus, in the illustration of FIGS. 1A and 1B, base portion 12 is on a right side of central axis 14, and is depicted the left side of the figure. A "unilateral coil" is defined as a coil wherein base portion 12 is positioned on one side of central axis 14. Return portion 32 may be positioned on the same side of central axis 14 as base portion 12, or on an opposite side of central axis 14, or both. Base portion 12 and return portion 32 are depicted schematically in FIGS. 1A and 1B as being straight-lined in shape. However, it should be readily apparent that other shapes are possible in accordance with embodiments of the present invention, as will be described further hereinbelow. In one embodiment, as shown in FIG. 1A, base portion 12 is positioned close to central axis 14, while return portion 32 is positioned at a distance from central axis 14. In another embodiment, as shown in FIG. 1B, base portion 12 is positioned at a distance from central axis 14, while return portion 32 is positioned close to central axis 14. Return portion 32 may be placed at a vertical distance and/or a horizontal distance from base portion 12, as will be described further hereinbelow.

Base portion 12 includes multiple stimulating elements 20, depicted in FIGS. 1A and 1B with arrows to illustrate the direction of electrical flow. Although arrows showing a direction of electrical flow of multiple stimulating elements 20 are depicted facing "down", it should be readily apparent that this designation is for illustrative purposes and should not be regarded as limiting. Thus, current flowing through multiple stimulating elements 20 may be in any direction relative to central axis 14 as determined by a shape of unilateral coil 10. Multiple stimulating elements 20 are shown as individual stimulating elements labeled first stimulating element 21, second stimulating element 22 and third stimulating element 23. It should be readily apparent that although three individual stimulating elements are shown in FIGS. 1A and 1B schematically, unilateral coil 10 may include any suitable number of stimulating elements and are not limited to the amounts shown herein. Multiple stimulating elements 20 are substantially parallel to one another and are spaced apart from one another by distances, wherein first and second stimulating elements 21 and 22 are separated by a first stimulating distance D1, second and third stimulating elements 22 and 23 are separated by a second stimulating distance D2, and so on. Stimulating distances D1, D2, etc. may be equal to one another or may vary in a random or periodic manner. The direction of electrical stimulation of each of stimulating elements 20 is substantially the same. That is, current flows through each of multiple stimulating elements 20 in a predetermined direction, and multiple stimulating elements 20 are nested within one another, such that current flows in substantially the same direction for each of stimulating elements 21-23 but separated by distances D1-D2.

Return portion 32 includes multiple return elements 40. Return elements 40 are depicted in FIGS. 1A and 1B with arrows to illustrate the direction of electrical flow. It should be readily apparent from FIGS. 1A and 1B that the direction of electrical flow for return elements 40 is opposite a direction of electrical flow for stimulating elements 20. Although arrows showing a direction of electrical flow of multiple return elements 40 are depicted facing "up", it should be readily apparent that this designation is for illustrative purposes and should not be regarded as limiting. Thus, current flowing through multiple return elements 40 may be in any direction relative to central axis 14 as determined by a shape of unilateral coil 10, provided that the direction of current flowing through multiple return elements 40 is substantially opposite (ie, 180 degrees) the direction of current flowing through multiple stimulating elements 20.

Multiple return elements 40 are shown as individual return elements labeled first return element 41, corresponding to first stimulating element 21, second return element 42 corresponding to second stimulating element 22, and third return element 43 corresponding to third stimulating element 23. It should be readily apparent that although three individual return elements are shown in FIGS. 1A and 1B schematically, unilateral coil 10 may include any suitable number of return elements and are not limited to the amounts shown herein. Generally, the number of return elements 40 corresponds to the number of stimulating elements 20. Multiple return elements 40 are substantially parallel to one another and are spaced apart from one another by distances, wherein first and second return elements 41 and 42 are separated by a first return distance D10, second and third return elements 42 and 43 are separated by a second return distance D11, and so on. Stimulating distances D10, D11, etc. may be equal to one another or may vary in a random or periodic manner. In some embodiments, stimulating elements 20 are electrically connected to return elements 40 via connecting elements 52. In some embodiments, connecting elements 52 may be substantially straight and may run in a direction which is substantially perpendicular to multiple stimulating elements 20 and multiple return elements 40, as shown in FIGS. 1A and 1B. In alternative embodiments, connecting elements 52 may be curved or have other configurations for connecting multiple stimulating elements 20 to multiple return elements 40.

Figure 2A:
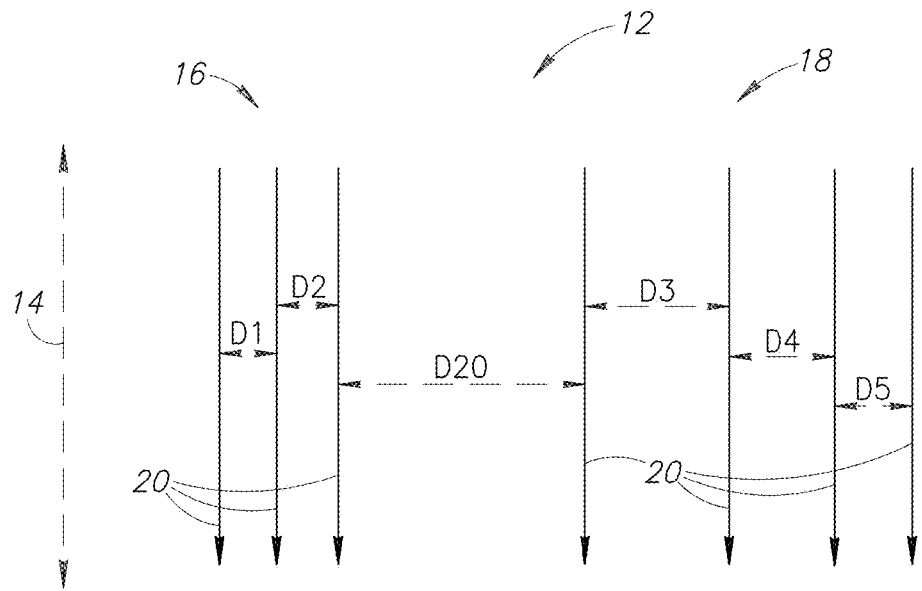
FIGS. 2A and 2B are schematic illustrations of a base portion of the unilateral coil of FIG. 1, in accordance with embodiments of the present invention.
Figure 2B:
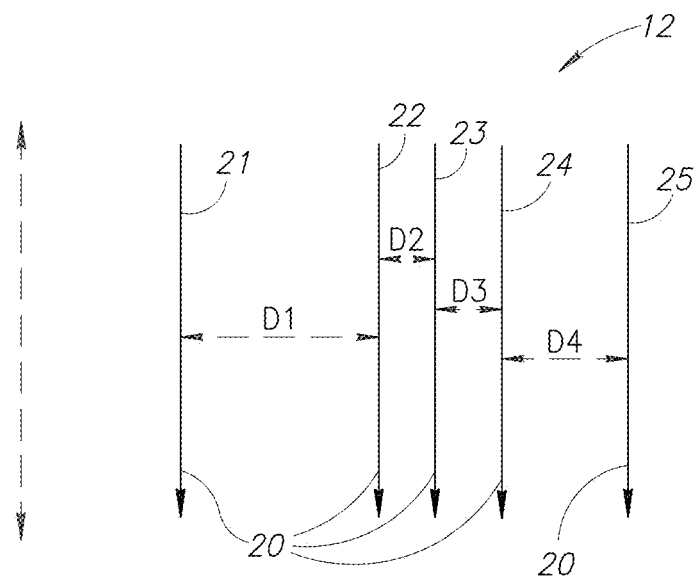

Reference is now made to FIGS. 2A and 2B, which are schematic illustrations of base portion 12 in accordance with embodiments of the present invention. In one embodiment, as shown schematically in FIG. 2A, base portion 12 includes a first base portion group 16 and a second base portion group 18. First base portion group 16 may be separated from second base portion group 18 by a first base portion group distance D20. In some embodiments, additional base portion groups may be included as well, and separated from one another by additional base portion group distances. Each base portion group is defined as a group by one of several criteria, including location, spacing, and connection to return elements. For example, first base portion group 16 may include multiple stimulating elements each separated by equal distances D1 and D2, while second base portion group 18 may include multiple stimulating elements separated from one another by equal distances D3, D4, D5, etc. wherein D1 and D2 are different than D3, D4, D5. In another embodiment, first base portion group 16 may be configured to be positioned on one portion of the head while second base portion group 18 may be configured to be positioned on another portion of the head. In yet another embodiment, first base portion group 16 may be connected to return elements which are in contact with the head and second base portion group 18 may be connected to return elements which are protruding from the head. It should be readily apparent that a direction of current flow in first base portion group 16 is substantially the same as a direction of current flow in second base portion group 18.

In some embodiments, as shown in FIG. 2B, base portion 12 may include stimulating elements 20 having distances between them which are variable. Thus, a distance D1 between first and second stimulating elements 21 and 22 is different than a distance D2 between second and third stimulating elements 22 and 23, etc.

Figure 3A:
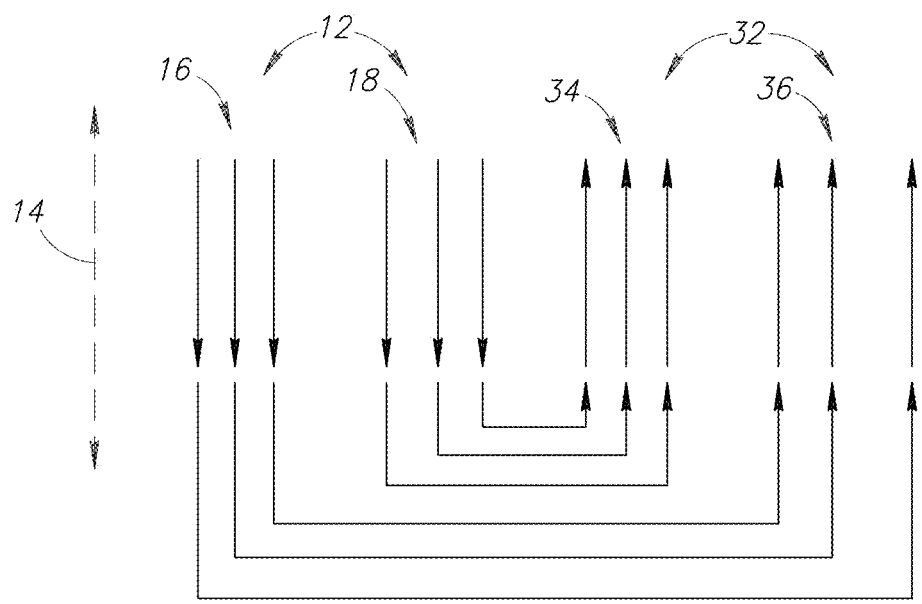
FIGS. 3A and 3B are schematic illustrations of base portions and return portions of the unilateral coil of FIG. 1, wherein the base and return portions have various configurations in accordance with embodiments of the present invention.
Figure 3B:
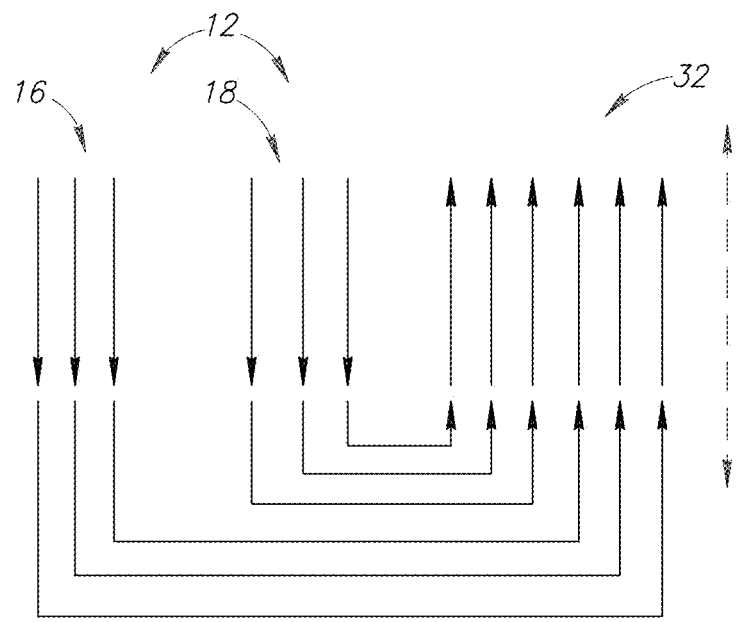

Similarly, return portion 32 may have multiple return portion groups. For example, as shown in FIG. 3A, base portion 12 may include a first base portion group 16 having a first configuration and a second base portion group 18 having a second configuration, and return portion 32 has a first return portion group 36 and a second return portion group 34. It should be readily apparent, as shown in FIG. 3A, that characteristics of first base portion group 16 do not necessarily match characteristics of first return portion group 36. For example, distances between multiple stimulating elements 20 may be different than distances between corresponding multiple return elements 40. In another embodiment, as shown in FIG. 3B, base portion 12 may include a first base portion group 16 having a first configuration and a second base portion group 18 having a second configuration, while return portion 32 has a single configuration for all of return elements 40.

Figure 4:
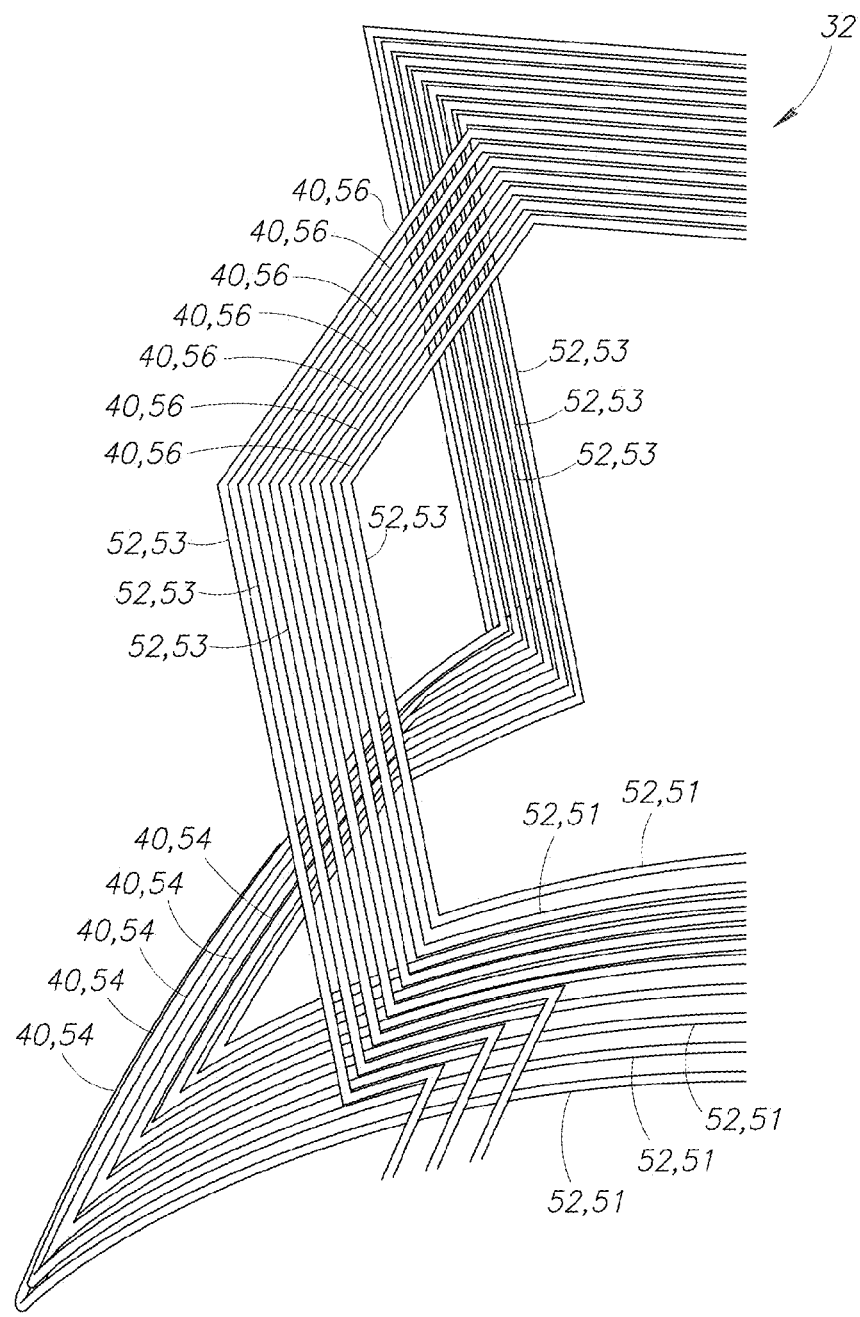
FIG. 4 is an illustration of a return portion of the unilateral coil of FIG. 1, in accordance with embodiments of the present invention.

Reference is now made to FIG. 4, which is an illustration of a return portion 32, in accordance with embodiments of the present invention. Depicted in FIG. 4 is a return portion 32 configured to be positioned on a side of the head, although it should be readily apparent that similar configurations of return portion 32 may be used for other areas, such as a rear portion of the head, for example. Return elements 40 are shown at two different heights, wherein some of return elements 40 are configured to be in contact with a body part and are on a same plane as base portion 12 (not shown). These return elements 40 are referred to as contacting return elements 54. Some of return elements 40 are configured to be protruding from the plane of base portion 12, and are referred to as protruding return elements 56. Protruding return elements 56 may be at a vertical distance or a horizontal distance from base portion 12, as long as protruding return elements 56 are configured to protrude from circular coil 10 such that they are configured not to contact the body part which base portion 12 is configured to contact. Thus, connecting elements 52 may be horizontal connecting elements 51 or may be vertical connecting elements 53 or may have additional configurations as needed to connect return portion 32 to base portion 12.

In some embodiments, some of multiple return elements 40 are contacting return elements 54 and some of multiple return elements 40 are protruding return elements 56. In some embodiments, all of multiple return elements 40 are contacting return elements 54. In some embodiments all of multiple return elements 40 are protruding return elements 56. Any combination of protruding and/or contacting return elements is possible and is included within the scope of the present invention.

Figure 5:
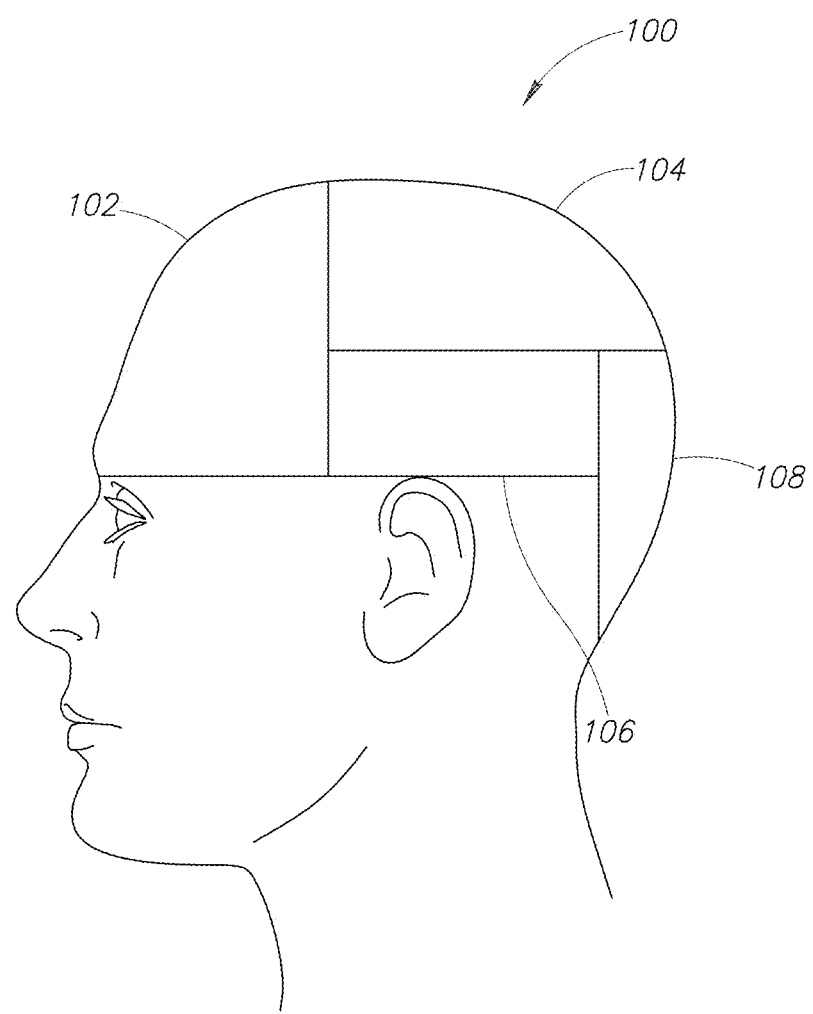
FIG. 5 is an illustration of anatomical sections of a head.

Reference is now made to FIG. 5, which is an illustration of anatomical sections of a head 100. For the purposes of illustrating the present invention, head 100 has four sections: a frontal section 102 at a front portion of head 100, a parietal section 104 to the rear of frontal section 102 and at a top portion of head 100, a temporal section 106 on the side of head 100 and an occipital section 108 at a rear portion of head 100. Unilateral coil 10 is configured such that base portion 12 with stimulating elements 20 are positionable on one side of a first section of head 100, and return portion 32 with return elements 40 are also positionable on the same side of the central axis 14. Thus, for example, base portion 12 may be positioned on frontal section 102, with central axis 14 running along an anterior-posterior central line. In another embodiment, base portion 12 may be positioned on temporal section 106, with central axis 14 running along a posterior-anterior central line. In yet another embodiment, base portion 12 may be positioned on parietal section 104, with central axis 14 running along a posterior-anterior central line. In yet another embodiment, base portion 12 may be positioned on frontal section 102, with central axis 14 running along a lateral-medial line. In this way, base portion 12 stimulates a section of the brain, while return portion brings returning current back at a section which is remote from the stimulated section of the brain. In some embodiments, both base portion 12 and return portion 32 are adjacent to the head, and in some embodiments, base portion 12 is adjacent to the head while return portion 32 is remote from the head. In some embodiments base portion 12 is adjacent to the head while some of return portion 32 elements are adjacent to the head and some of return portion 32 elements are remote from the head. In some embodiments, connecting elements 52 are adjacent to the head and in other embodiments, connecting elements 52 are remote from the head. Yet in other embodiments some of connecting elements 52 are adjacent to the head and some of them are remote from the head.

Figure 6:
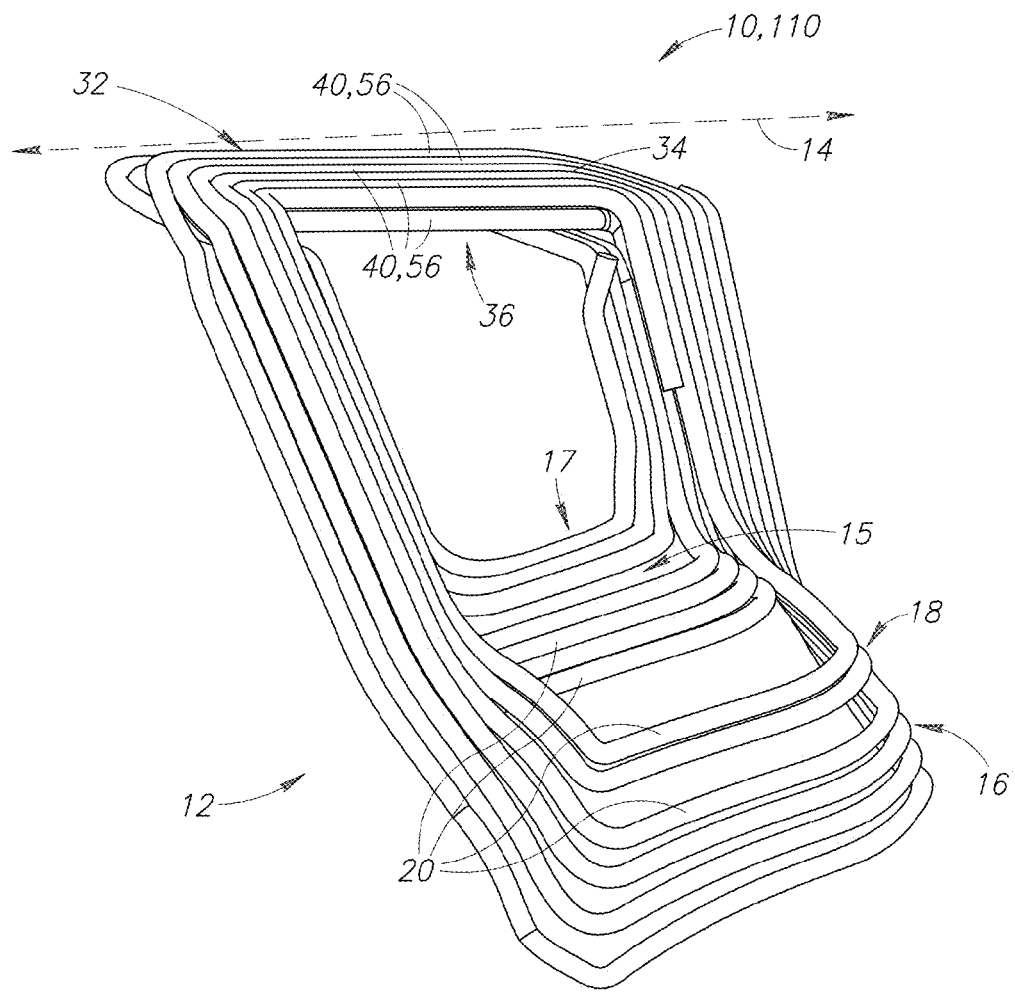
FIG. 6 is a perspective illustration of a coil, which is an example of the unilateral coil of FIG. 1, in accordance with embodiments of the present invention.

Reference is now made to FIG. 6, which is a perspective illustration of a coil 110, which is an example of a unilateral coil 10 in accordance with embodiments of the present invention. Coil 110 includes a base portion 12 having a first base portion group 16 of multiple stimulating elements 20, a second base portion group 18 of multiple stimulating elements 20, a third base portion group 15 of multiple stimulating elements 20 and a fourth base portion group 17 of multiple stimulating elements 20. Coil 110 further includes a return portion 32 including return elements 40 corresponding to multiple stimulating elements 20. Return portion 32 also includes a first return portion group 34 corresponding to first and second base portion groups 16 and 18, and a second return portion group 36 corresponding to third and fourth base portion groups 15 and 17. In the embodiment shown herein, base portion 12 is configured to be positioned on a frontal section 102 and temporal section 106 of head 100 and return portion 32 is configured to be positioned above head 100, close to central axis 14. Multiple return elements 40 are protruding return elements 56.

Coil 110 is used to stimulate left or right lateral and medial prefrontal cortex (PFC) brain regions. In one embodiment, a left coil 110 can be used to activate neural structures in the left PFC without activating the right PFC. This type of coil has shown in preliminary studies to improve depression measures. Such a coil may be useful for a variety of brain disorders including depression, bipolar disorder, schizophrenia (including negative symptoms of schizophrenic patients), attention deficit and hyperactivity disorder (ADHD) and more.

Figure 7:
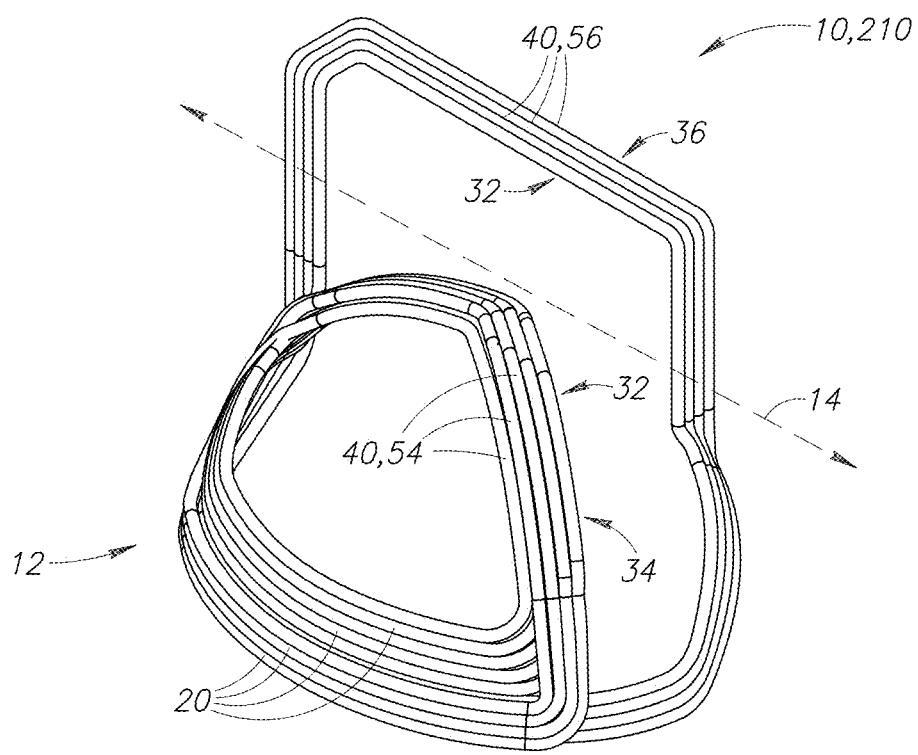
FIG. 7 is a perspective illustration of a coil, which is an example of the unilateral coil of FIG. 1, in accordance with embodiments of the present invention.

Reference is now made to FIG. 7, which is a perspective illustration of a coil 210, which is an example of a unilateral coil 10 in accordance with embodiments of the present invention. Coil 210 includes a base portion 12 having multiple stimulating elements 20. Multiple stimulating elements 20 are configured to be positioned on a temporal section 106 of head 100. Coil 210 further includes a return portion 32 having a first return portion group 34 and a second return portion group 36. First return portion group 34 is configured to be positioned on a parietal portion 104 of head 100 and is separated from base portion 12 by a distance of at least 4 cm. First return portion group 34 is configured to contact the head, and thus includes contacting return elements 54. Second return portion group 36 includes multiple return elements 40 which are protruding return elements 56.

Coil 210 is used to stimulate only right or left temporal brain regions such as the insula and entorhinal cortex and may be useful for treating, for example, auditory hallucinations in schizophrenia and all sorts of addiction such as drug addiction, cigarette addiction, gambling, obesity and eating disorders.

Figure 8:
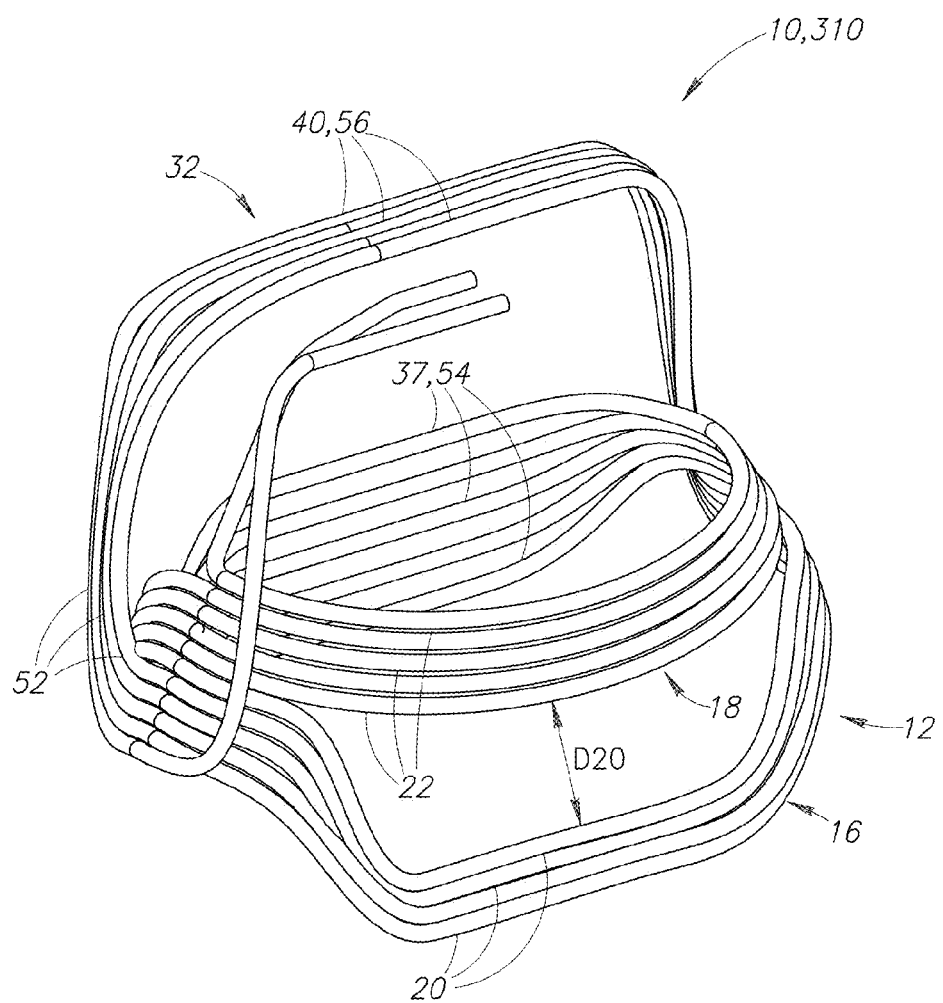
FIG. 8 is a perspective illustration of a coil, which is an example of the unilateral coil of FIG. 1, in accordance with embodiments of the present invention.

Reference is now made to FIG. 8, which is a perspective illustration of a coil 310, which is an example of a unilateral coil 10 in accordance with embodiments of the present invention.

Coil 310 includes a base portion 12 having a first base portion group 16 of first multiple stimulating elements 20 and a second base portion group 18 of second multiple stimulating elements 22. Coil 310 further includes a return portion 32 including first return elements 40, corresponding to first multiple stimulating elements 20 and second return elements 37, corresponding to second multiple stimulating elements 22. In the embodiment shown herein, first return elements 40 are protruding return elements 56, and second return elements 37 are contacting return elements 54. In the embodiment shown herein, base portion 12 is configured to be positioned on a parietal section 104 and a temporal section 106 of head 100 and return portion 32 is configured to be positioned above head 100. First base portion group 16 is positioned below second base portion group 18 and is separated from second base portion group 18 by a distance D20. Protruding return elements 56 are configured to protrude from head 100. Connecting elements 52 may run along a frontal section of head 100.

Figure 9A:
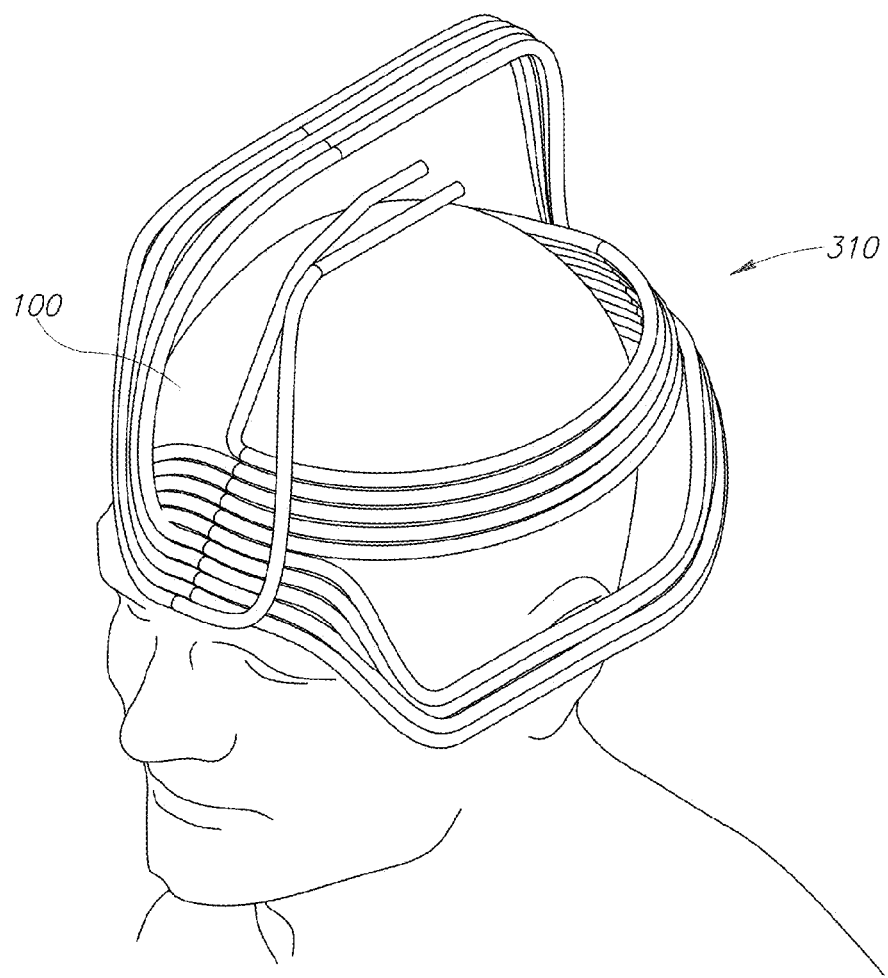
FIGS. 9A and 9B are perspective illustrations of the coil of FIG. 8, shown in position on a head.
Figure 9B:
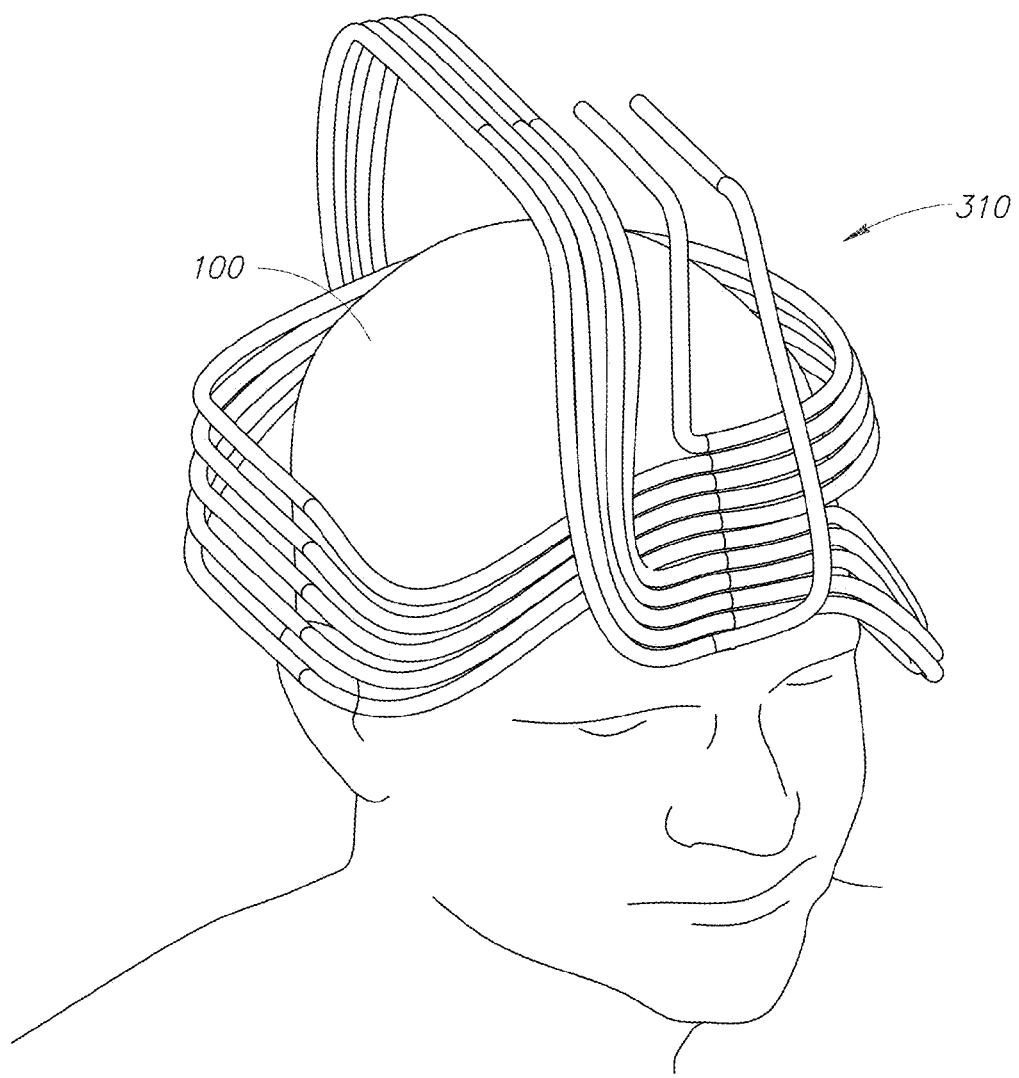

Reference is now made to FIGS. 9A and 9B, which are illustrations showing coil 310 positioned on a right side of head 100, as viewed from the right side and from the left side, respectively.

Coil 310 is used to stimulate temporal lobe brain regions on either right or left hemisphere, and may be useful for treating, for example, epilepsy.

EXAMPLES

Figure 10:
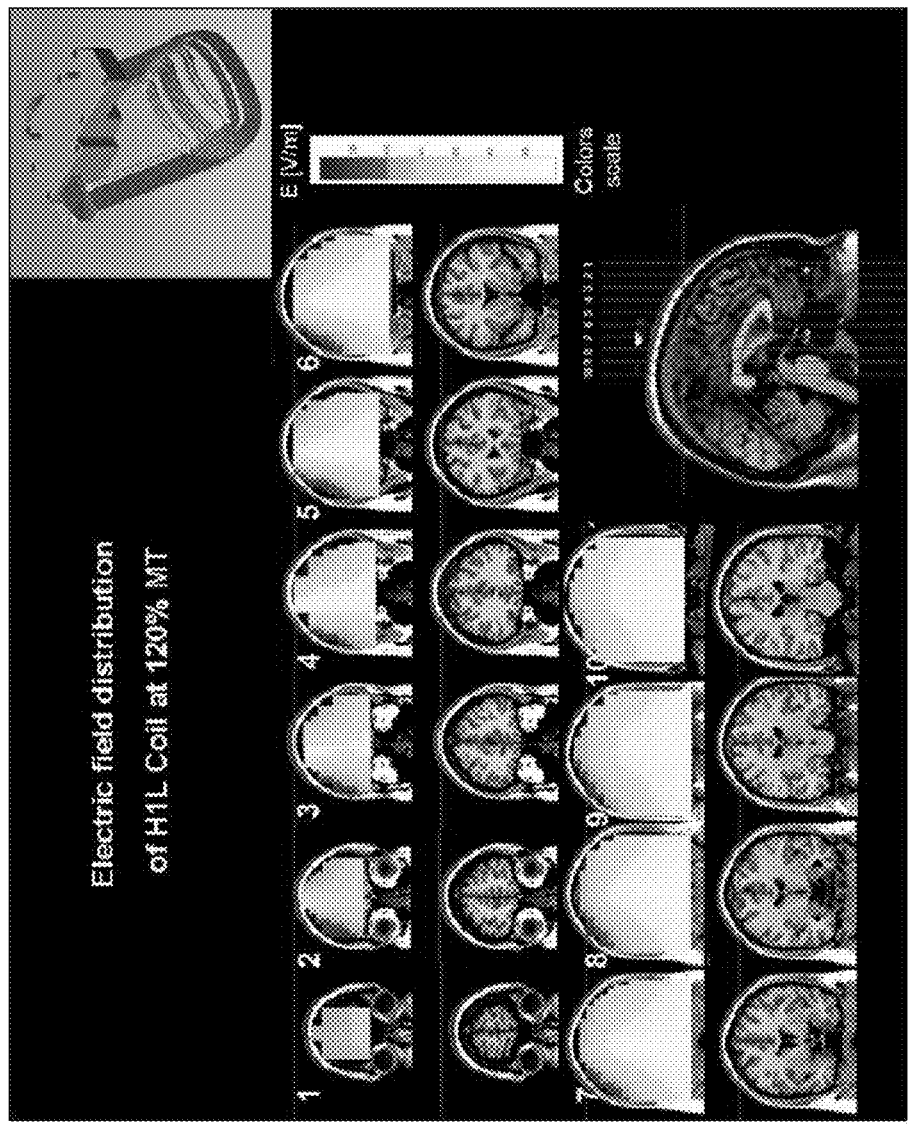
FIG. 10 is an illustration of electric field distribution maps of the coil of FIG. 6 as measured in a human head phantom model.

Reference is now made to FIG. 10 which presents electric field distribution maps_of coil 110 of FIG. 6. The field distribution produced by coil 110 was measured in a human head phantom model. The probe was moved in three directions inside the phantom model using a displacement system with 1 mm resolution, and the field distribution of the coil was measured in the whole head model volume in 1 cm resolution. Axial and coronal field maps were produced. The field maps were superimposed on anatomical T1-weighted MRI coronal slices, to show the induced field in each anatomical brain region. The field maps are shown for stimulator output set at 120% of threshold. The dark pixels indicate field magnitude above the threshold for neuronal activation. The threshold was set to 100 V/m, which is within the accepted range of thresholds required for hand motor activation. The intensity of stimulator power output used for drawing the maps representing the distribution of the electric field for each coil was set to the level required to obtain 120% of the neural motor threshold, at a depth of 1.5 cm, according to the approximate depth of hand motor cortex sites. It can be seen that when placing the coil over the prefrontal cortex, supra-threshold field is induced at left lateral prefrontal, medial prefrontal and orbitofrontal regions.

Figure 11:
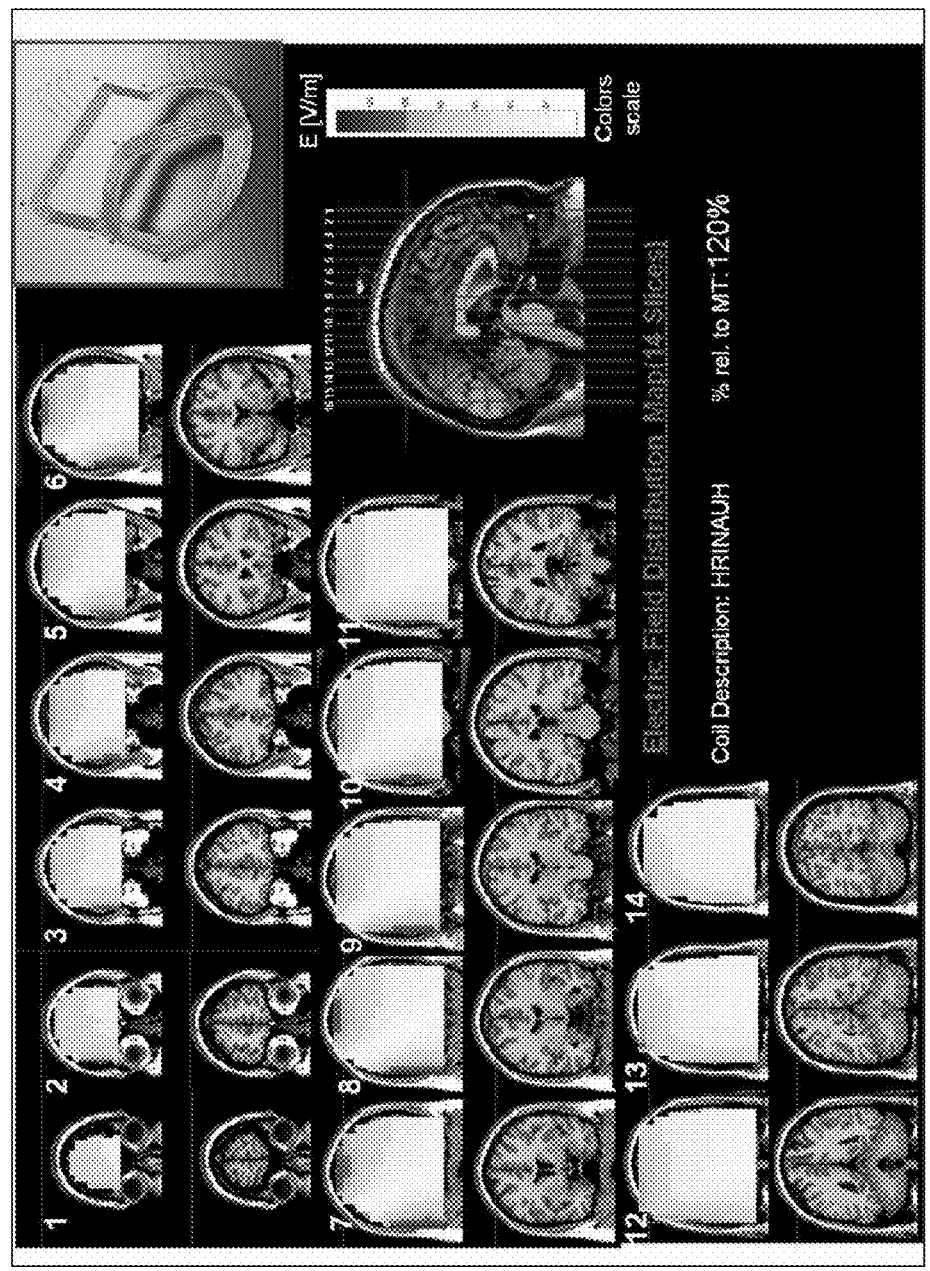
FIG. 11 is an illustration of electric field distribution maps of the coil of FIG. 7 as measured in a human head phantom model.

Reference is now made to FIG. 11 which presents electric field distribution maps_of coil 210 of FIG. 7. The field distribution produced by coil 210 was measured using the same method as for FIG. 10. The field maps are shown for stimulator output set at 120% of motor threshold. It can be seen that when placing the coil over the right temporal cortex, supra-threshold field is induced at right temporal regions including the right insula.

Figure 12:
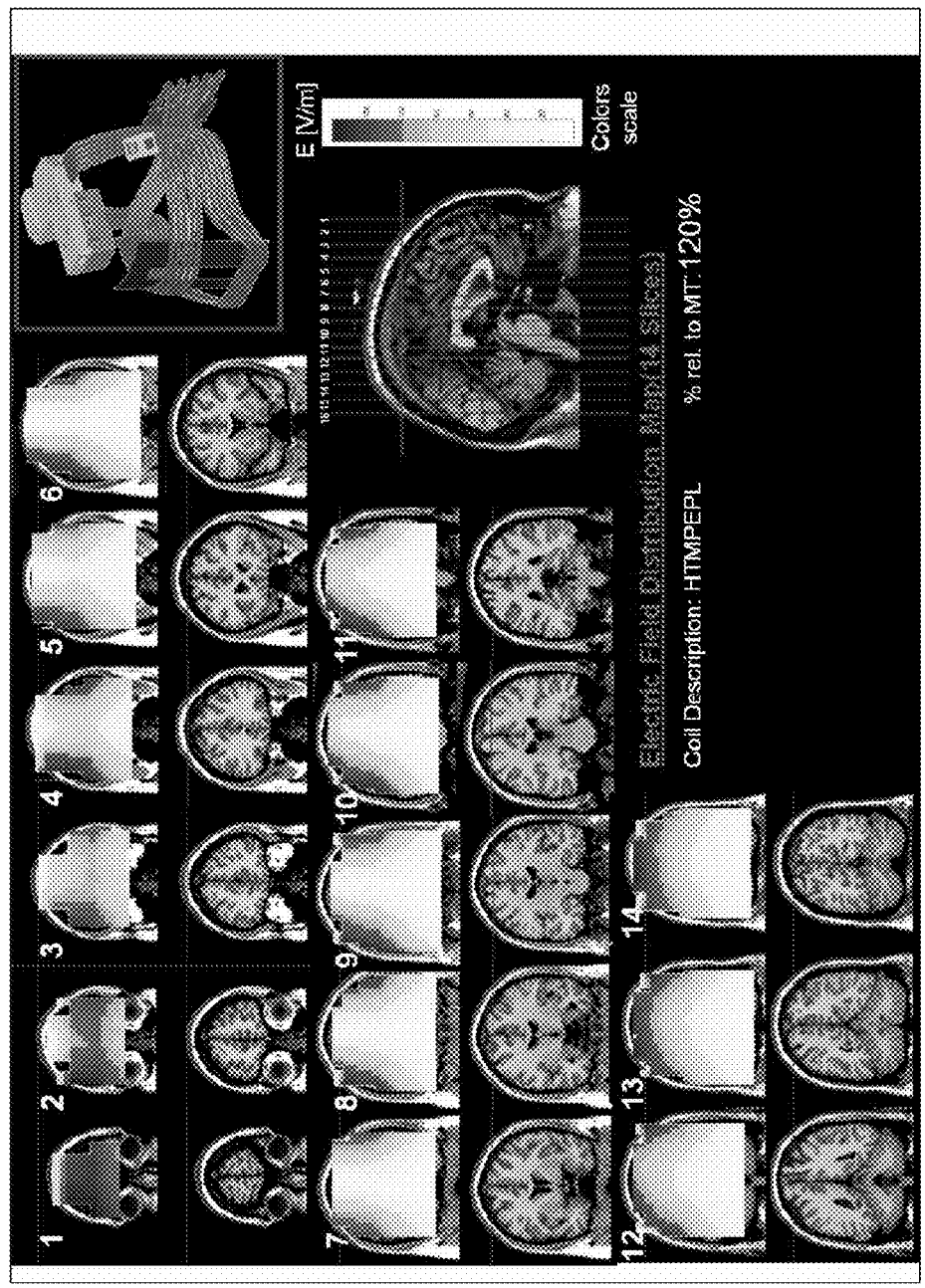
FIG. 12 is an illustration of electric field distribution maps of the coil of FIG. 8 as measured in a human head phantom model.

Reference is now made to FIG. 12 which presents electric field distribution maps_of coil 310 of FIG. 8. The field distribution produced by the coil 310 was measured using the same method as for FIG. 10. The field maps are shown for stimulator output set at 120% of motor threshold. It can be seen that when placing the base portion of the coil over the right temporal cortex, supra-threshold field is induced at right temporal regions including deeper regions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

What is claimed is:

1. A method of treating a disease, the method comprising:
    placing a unilateral coil on a head, said unilateral coil including a base portion having multiple spaced apart stimulating elements configured to carry electrical current in substantially a first direction when said unilateral coil is positioned on only one side of the head, and wherein each of said multiple stimulating elements is tangential to the head, and a return portion having multiple return elements, wherein each of said multiple return elements corresponds to one of said multiple stimulating elements, and wherein each of said multiple return elements is configured to carry electrical current in substantially a second direction, wherein said second direction is an opposite direction to said first direction, wherein said return portion is spaced a distance away from said base portion;
    positioning said unilateral coil on the head such that said base portion is only on one temporal portion of the head, and such that said multiple stimulating elements are tangential to the head when positioned thereon and such that said return portion is substantially along a midline of a sagittal plane of the head and protruding therefrom; and
    stimulating a brain region in the head using said unilateral coil.

2. The method of claim 1, wherein said treating a disease comprises treating at least one of: depression, bipolar disorder, schizophrenia, ADHD, drug addiction, cigarette addiction, alcoholism, gambling problem, eating disorders, obesity, autism, Asperger's disease, epilepsy.

3. The method of claim 1, wherein said stimulating comprises stimulating only a right or a left temporal brain region.

4. The method of claim 1, wherein said stimulating is done at 120% of motor threshold.

* * * * *